(12) United States Patent
Kaercher et al.

(10) Patent No.: US 9,095,365 B2
(45) Date of Patent: Aug. 4, 2015

(54) HANDLING DEVICE FOR A MICRO-INVASIVE SURGICAL INSTRUMENT

(75) Inventors: Daniel Kaercher, Radolfzell (DE); Jochen Stefan, Wald (DE)

(73) Assignee: KARL STORZ GMBH & CO. KG (DE)

( * ) Notice: Subject to any disclaimer, the term of this patent is extended or adjusted under 35 U.S.C. 154(b) by 55 days.

(21) Appl. No.: 13/444,490

(22) Filed: Apr. 11, 2012

(65) Prior Publication Data

US 2012/0259358 A1 Oct. 11, 2012

(30) Foreign Application Priority Data

Apr. 11, 2011 (DE) .......................... 10 2011 007 119

(51) Int. Cl.
*A61B 17/00* (2006.01)
*A61B 17/29* (2006.01)

(52) U.S. Cl.
CPC ......... *A61B 17/29* (2013.01); *A61B 2017/0046* (2013.01); *A61B 2017/00455* (2013.01); *A61B 2017/292* (2013.01); *A61B 2017/293* (2013.01); *A61B 2017/2903* (2013.01); *A61B 2017/2929* (2013.01)

(58) Field of Classification Search
CPC ..................... A61B 17/29; A61B 2017/00455; A61B 2017/0046; A61B 2017/2903; A61B 2017/292
USPC ..................................................... 606/205, 1
See application file for complete search history.

(56) References Cited

U.S. PATENT DOCUMENTS

| 5,308,358 A * | 5/1994 | Bond et al. ..................... 606/205 |
|---|---|---|
| 7,708,758 B2 * | 5/2010 | Lee et al. ..................... 606/205 |
| 2001/0041911 A1 | 11/2001 | Dittrich et al. |
| 2002/0087048 A1 | 7/2002 | Brock et al. |
| 2004/0230221 A1 | 11/2004 | Gadberry et al. |
| 2006/0025792 A1 | 2/2006 | Gibson et al. |
| 2006/0074432 A1 * | 4/2006 | Stad et al. ....................... 606/90 |
| 2008/0294192 A1 * | 11/2008 | Stefan et al. ................... 606/205 |

FOREIGN PATENT DOCUMENTS

| DE | 19722062 A1 | 12/1998 |
|---|---|---|
| DE | 19853305 C1 | 10/2000 |
| DE | 102006038515 A1 | 2/2008 |
| DE | 102006038516 A1 | 2/2008 |
| DE | 102008015418 A1 | 9/2009 |
| DE | 102008052623 A1 | 4/2010 |
| EP | 1622521 B1 | 1/2011 |
| WO | 2010064050 A1 | 6/2010 |

OTHER PUBLICATIONS

DE Search Report Application No. 10 2011 007 119.9 Date: Oct. 25, 2012 5 pages.
European Search Report; Application No. EP 12 00 2393; Issued: Jul. 17, 2012; Mailing Date: Jul. 24, 2012; 5 pages.

* cited by examiner

*Primary Examiner* — Victor Nguyen
*Assistant Examiner* — Sarah Simpson
(74) *Attorney, Agent, or Firm* — Whitmyer IP Group LLC

(57) ABSTRACT

A handling device for a micro-invasive surgical instrument includes a gripping device to manually hold and guide the handling device, a shaft coupling to detachably mechanically couple the handling device with a proximal end of a shaft, a rod coupling that can slide inside the handling device for detachable mechanical coupling with a proximal end of a transmission rod that can be slid inside a shaft coupled with the shaft coupling, and an orientation device to rotate a proximal end of a transmission rod, which has been inserted into the handling device, into a predetermined orientation or into one of several predetermined orientations.

10 Claims, 3 Drawing Sheets

HANDLING DEVICE FOR A MICRO-INVASIVE SURGICAL INSTRUMENT

CROSS-REFERENCE TO RELATED APPLICATIONS

The present application claims priority of German patent application No. 10 2011 007 119.9 filed on Apr. 11, 2011, the content of which is incorporated herein by reference.

FIELD OF THE INVENTION

The present invention relates to a handling device for a micro-invasive surgical instrument, a micro-invasive surgical instrument and thereby, in particular, to characteristics for coupling a shaft and a transmission rod with the handling device.

BACKGROUND OF THE INVENTION

Many micro-invasive surgical instruments include a long, thin shaft, a tool on the distal end of the shaft and a handling device on the proximal end of the shaft. The tool includes, for example, a grasping, dissecting, biopsy or other forceps, a scissors or a needle holder with at least two straight or curved clamps, cutting edges or other jaw members of which at least one is movable. Alternatively, the tool includes another active device, for example a manipulator with a finger or a finger-shaped device or an electrode in hook form or other shape. The shaft contains (at least) one transmission rod, which as a rule is mounted in a closed channel in the interior of the shaft. The handling device includes one or more actuation devices that can move with respect to one another, for example two gripping parts, that medical staff can move in relation to one another with one hand. The proximal end and the distal end of the transmission rod are coupled with the actuation device or with the tool in such a way that a force exerted by medical staff onto the actuation devices or a relative movement of the actuation devices caused by medical staff can be transmitted to the tool, for example to move clamps toward one another or to press them together.

In using a micro-invasive surgical instrument of this type, the tool and a part of the shaft are inserted into a natural or artificial cavity in the patient's body, for example through a natural or artificial bodily opening. The development of micro-invasive surgical techniques tends toward using constantly smaller and, especially, fewer means of access. For example, in order to be able to work with an endoscope and two instruments in laparoscopic surgery by way of a single trocar, instruments with curved shafts can be used. An instrument with a curved shaft, however, cannot always be easily rotated around its longitudinal axis inside the access way in order to modify the orientation of the tool at its distal end.

In patent DE 10 2006 038 516 A1, a tubular medical instrument is described in which a tool 5, a shaft 3 and a handle 2 can be separated from one another for cleaning.

Patent DE 10 2008 015 418 A1 discloses a medical instrument with a curved shaft. A jaw member is detachably connected with a shaft by means of a bayonet lock. In connected position, the jaw member can be rotated with respect to the shaft. The shaft is detachably connected with a handle. The curved shaft can be rotated with respect to the handle by means of a hand wheel that is connected with an external shaft tube in torque-proof manner. An inside tube is connected to the handle with an additional hand wheel. The instrument can be configured as a unipolar or bipolar HF instrument.

Patent DE 10 2008 052 623 A1 discloses a surgical instrument with a jaw unit, a shaft and a gripping unit. The jaw unit is detachably affixed to the end of a shaft tube of the shaft and can rotate with respect to it.

To allow easy, thorough cleaning of the instrument, the tool, shaft and handling device of a micro-invasive surgical instrument, without use of auxiliary means, ought to be separable from one another and capable of being combined or coupled with one another. It is known, for example, from DE 10 2006 038 516 A1 how to configure the tool and the distal end of the shaft in such a way that the tool can be assembled and disassembled in a fully open assembled position. However, a few aspects both of the coupling of the tool with the shaft and of the coupling of the shaft with the handling device have not been sufficiently satisfactorily resolved to date, especially concerning the ability of the tool to turn or rotate with respect to the shaft when in coupled state.

SUMMARY OF THE INVENTION

An object of the present invention comprises in providing an improved tool for a micro-invasive surgical instrument and an improved micro-invasive surgical instrument.

This object is fulfilled through the content of the independent claims.

Refinements are indicated in the dependent claims.

Embodiments of the present invention are based on the idea of providing, with a handling device, an orientation device that makes it possible to insert the proximal end of a shaft, with a non-rotation-symmetrical proximal end of a transmission rod, without regard for its orientation, into the handling device. For this purpose the orientation device is configured in such a way that a proximal end of a transmission rod inserted in any desired manner with regard to a rotation around its longitudinal axis is moved, in particular rotated or turned, into a predetermined orientation or into one of several predetermined orientations. As a rule, the orientation device comprises one or more dead zones with respect to the original orientation of the proximal end of the transmission rod. Between these dead zones, however, there are one or more large angle areas within which the proximal end of the transmission rod can originally be oriented as desired and then can be moved by the orientation device into one or more predetermined orientations.

A handling device for a micro-invasive surgical instrument includes a gripping device to manually hold and guide the handling device, a shaft coupling for detachable mechanical coupling of the handling device with a proximal end of a shaft, a rod coupling that can be at least either slid or rotated in the handling device for detachable mechanical coupling with a proximal end of a transmission rod that can be at least either slid or rotated in a shaft coupled with the shaft coupling, and an orientation device to rotate a proximal end of a transmission rod, inserted in the handling device, into a predetermined orientation or into one of several predetermined orientations.

The rod coupling, in particular, can be slid between a predetermined distal installation position and a working range of positions situated proximally from the predetermined installation position. The predetermined working range can be extended, in particular extended over several millimeters. Alternatively the working range can be small or—within the achievable or applied precision—can include only one position. In addition to the aforementioned installation position, additional installation positions can be foreseen within a particular related interval or range (installation range).

The rod coupling is mechanically coupled in particular with a manually movable actuation device of the handling device in order to transmit a manual translational or rotational movement of the actuation device and a force manually exerted on the actuation device and/or a torque manually exerted on the actuation device to the transmission rod, by means of which the movement and the force or torque is transmitted to the distal end of the transmission rod.

The rod coupling here is, in particular, configured in such a way that in the installation position it can enclose or release a proximal end of a transmission rod and can hold a proximal end of a transmission rod in positions within the working range with little play and, in particular, in a form-locked and/or force-locked connection.

The proximal end of a transmission rod, for which the handling device is foreseen and configured, can have a cross-section that is constant within a predetermined range. Torque between the orientation device and/or the rod coupling on the one hand and the proximal end of the transmission rod on the other hand can be transmitted by form-locking through a non-rotation-symmetrical cross-section of the proximal end of the transmission rod. A translational movement and a corresponding force can be transmitted by force-locking or friction-locking between the rod coupling and the proximal end of the transmission rod. A pressure force or pushing force in the distal direction can also be transmitted by form-locking to the proximal end of the transmission rod.

If the proximal end of the transmission rod has a non-constant cross-section in the area foreseen for an arrangement in the rod coupling, a translational movement and a corresponding force can be transmitted alternatively or in addition in form-locked manner between the rod coupling and the proximal end of the transmission rod. In particular, the proximal end of the transmission rod comprises one or more indentations and/or recesses in which the rod coupling can engage.

The rod coupling, in particular, can slide parallel to a longitudinal axis of a shaft that is coupled or to be coupled with the handling device. Alternatively or in addition, the rod coupling can rotate around a longitudinal axis of a shaft that is coupled or to be coupled with the handling device. The transmission rod is pliable in particular when a shaft that is coupled or to be coupled with the handling device is curved at least in part and/or is elastically curvable at least in portions. The transmission rod, however, is rigid or inelastic, especially in the longitudinal direction and/or with respect to torsion.

The orientation device is mounted distally forward, particularly as a separate component of the rod coupling. The orientation device can be a component of the rod coupling, so that it is positioned in particular on its distal site. The orientation device is configured in particular to rotate a proximal end of a transmission rod, which is oriented freely with respect to rotation around its longitudinal axis within one or more predetermined angle areas, into the predetermined orientation or into one of several predetermined orientations upon insertion in the handling device. Between the predetermined angle areas there can be dead zones that in practice can have a certain extension. If the original orientation of a transmission rod inserted into the handling device lies in one of the dead zones, the insertion of the transmission rod is hampered, and the proximal end of the transmission rod is not rotated into the predetermined orientation or into one of several predetermined orientations. The orientation device can be configured, however, so that the dead zones are smaller or essentially smaller than the predetermined angle areas between the dead zones.

The handling device and the orientation device are, in particular, configured in such a way that the proximal end of a tension rod can be inserted into the handling device in a direction parallel to its longitudinal axis. The longitudinal axis of a shaft, of a transmission rod or of a proximal end of a shaft or transmission rod means, in particular, the axis to which the concerned object is rotation symmetrical or essentially rotation symmetrical. In the case of a curved shaft or a pliable transmission rod, these statements apply in particular to their ends, which as a rule are straight or not curved, at least in portions.

In the predetermined orientation or in the predetermined orientations, the proximal end of the tension rods in each case can be detachably mechanically coupled with the rod coupling.

The orientation device can markedly simplify the handling of an entire micro-invasive surgical instrument, in particular in assembling or mechanically combining or coupling components. Medical or other staff—particularly after assembly of a tool on the distal end of a shaft—can insert the shaft with the transmission rod into the handling device without concern for the orientation of the proximal end of the transmission rod. If the orientation of the proximal end of the transmission rod happens to lie in a dead zone, this can be easily perceptible because the shaft cannot be inserted into the handling device up to the expected position. In this case it suffices to rotate the shaft and transmission rod by an angle that can be as small as desired, and the assembly can be continued and concluded. The shaft and transmission rod can therefore be inserted into the handling device quickly and without visual control. The handling device described here can thus improve staff efficiency and productivity. The medical staff's concentration on an activity that is essentially peripheral is no longer required and can be directed more completely to the patient and the treatment.

The orientation device particularly comprises a pass-through opening that extends from the distal to the proximal side, and the cross-section of said opening continuously varies in the direction from distal to proximal, at least in portions.

The cross-section of the pass-through opening, in particular, narrows in the direction from distal to proximal. Distally, the pass-through opening receives the proximal end of a transmission rod, in particular in a freely selected orientation. In the direction from distal to proximal, the cross-section of the pass-through opening varies in such a way that a proximal end of a transmission rod, originally with a freely selected orientation within a predetermined angle range, is rotated in a movement from the distal to the proximal side into a predetermined orientation. For this purpose the cross-section of the pass-through opening varies, in particular continuously or continuously in portions.

The pass-through opening of the orientation device particularly comprises a gliding surface that is not parallel to the direction in which a shaft and a transmission rod are to be inserted in the handling device. In particular, several gliding surfaces are foreseen. Each gliding surface can be level or screw-shaped in order, during a movement of a proximal end of a transmission rod from distal to proximal side in the pass-through opening, to cause a rotation into a predetermined orientation or into one of several predetermined orientations.

For example, the orientation device in the pass-through opening comprises two level gliding surfaces, so that the pass-through opening narrows like a wedge from the distal to the proximal end. The distance between the two gliding surfaces at the distal end of the pass-through opening in particular, is selected so that the proximal end of a transmission rod can be inserted in any selected orientation at the distal end into the pass-through opening. At the proximal end the two gliding surfaces, in particular, are at a distance from one another that is selected so that a proximal end of a transmission rod can be completely passed through the pass-through opening only in two predetermined orientations that differ from one another by 180 degrees.

The pass-through opening can alternatively be configured at the distal end in such a way that the proximal end of a transmission rod can be inserted into the pass-through opening only in an orientation within one or more angle ranges, and a proximal end of a transmission rod with an orientation within one or more small, predetermined dead zones cannot be inserted into the pass-through opening.

Glide surfaces, in particular those that are level and run into one another in wedge form, can be easily producible means to automatically rotate a proximal end of a transmission rod into a predetermined orientation and can achieve a reliable effectiveness along with low production costs.

With a handling device as described here, the orientation device can be slidable with respect to the rod coupling between a predetermined distal installation position and a predetermined proximal working position.

In particular, the orientation device can be slidable in a direction parallel to the longitudinal axis of a proximal end of a transmission rod that is inserted or is to be inserted into the handling device. As becomes clear hereafter and on the basis of the embodiments, a slidable orientation device can assume or comprise additional functions and thus encourage simple, compact structure of the handling device.

A handling device with an orientation device that can be slid between an installation position and a working position can be configured in such a way that the orientation device holds the rod coupling locked in the predetermined proximal working position.

As mentioned, the rod coupling can be slid, in particular, between a distal installation position and a working area or range of working areas that are situated proximally from the installation position, in particular parallel to the direction in which the orientation device is slidable. The handling device is configured in such a way that the orientation device in the predetermined proximal working position restricts the slidability of the rod coupling to the working area. The orientation device restricts the working range in particular because the rod coupling in the outermost distal position within the working range is in fact contiguous with the orientation device in its predetermined proximal working position.

A handling device with an orientation device that can be slid between an installation position and a working position can, in addition, comprise a shaft-locking device to lock a shaft on the shaft coupling, such that the handling device is configured in such a way that a shaft that is locked on the shaft coupling by the shaft locking device holds the orientation device in the predetermined proximal working position in which the orientation device holds the rod coupling locked.

In particular, in so doing, the proximal end of the shaft held by the shaft-locking device in a predetermined position impacts a distal side of the orientation device and thus holds said orientation device in the predetermined working position. The shaft-locking device thus cannot only hold the shaft directly in a predetermined position on the shaft coupling but also simultaneously can directly hold the rod coupling locked by the orientation device.

With a handling device as described here, the rod coupling in particular includes a movable gripping clamp to hold a proximal end of a transmission rod, such that the rod coupling is configured in such a way that the gripping clamp, with the rod coupling in a predetermined installation position, can enclose or release a proximal end of a transmission rod and can hold a proximal end of a transmission rod in a predetermined working range of positions of the rod coupling.

The rod coupling particularly includes two or more symmetrically positioned gripping clamps. Alternatively, the rod coupling includes only one gripping clamp or an asymmetrical arrangement of gripping clamps. Each gripping clamp can pivot in particular around a disposed axis between an installation position and a holding position. With the gripping clamp or gripping clamps in installation position, a proximal end of a transmission rod can be inserted in the rod coupling and can be removed from it. With the gripping clamp or gripping clamps in holding position, a proximal end of a transmission rod can be held in form-locked and/or force-locked and or friction-locked manner by the gripping clamp or gripping clamps.

In particular, the gripping clamp or gripping clamps are configured in order to include a claw or a portion with an enlarged cross-section on the proximal end of a transmission rod in order to constitute a form-locked connection with the proximal end of the transmission rod. In somewhat more general terms, the gripping clamp can comprise a concave area in which a corresponding convex area on the proximal end of the transmission rod can engage. Alternatively, the gripping clamp or gripping clamps can be configured to engage in a tapering or a concave area on or near the proximal end of the transmission rod in order to constitute a form-locked connection with the proximal end of the transmission rod. In addition, both the gripping clamp or clamps and the proximal end of the transmission rod can each comprise a convex area (or several convex areas) and a concave area (or several concave areas), such that in each case a convex area is configured on the gripping clamp in order to engage in a concave area on the proximal end of the transmission rod, and such that in each case a convex area is configured on the proximal end of the transmission rod in order to engage in a concave area on the gripping clamp.

The handling device can also include a guide pin and a control groove, so that either the guide pin or the control groove is positioned on the gripping clamp and so that the guide pin engages in the control groove in order to hold the gripping clamp in various positions independently of the position of the rod coupling.

In particular, the guide pin and control groove are configured and positioned in such a way that, with the rod coupling in installation position, the gripping clamp is pivoted away from the foreseen position of a proximal end of a transmission rod and is pivoted into positions in the predetermined working range toward the proximal end of the transmission rod and is in form-locked connection with the transmission rod. In particular, the control groove on the handling device cannot be slid in the direction of slidability of the rod coupling and the guide pin is positioned on the gripping clamp.

The control groove can be rotatable with the entire rod coupling and, in some cases, with the orientation device, in particular around the longitudinal axis of a proximal end of a transmission rod that is inserted or is to be inserted into the rod coupling. In the case of several gripping clamps, each gripping clamp in particular comprises one or more guide pins. The gripping clamp or each of several gripping clamps comprises in particular two guide pins opposite one another, which engage in control grooves that are opposite and running parallel.

With a handling device as described here, the orientation device can rotate, in particular with respect to the handling device, around an axis so that the orientation device in addition is configured to transmit torque to a transmission rod coupled with the rod coupling.

In particular, the orientation device can rotate around a longitudinal axis of a proximal end of a shaft that is inserted into the handling device or of a proximal end of a transmission rod in the shaft. To transmit torque to a transmission rod coupled with the rod coupling, the orientation device, particularly on its proximal end, is configured by form-locking with the proximal end of the expected transmission rod. For example, the proximal end of the transmission rod comprises a flattening with two parallel surfaces at a predetermined distance apart, and the orientation device on its proximal end comprises two surfaces opposite one another at the predetermined distance or at a slightly greater distance.

The orientation device is, in particular, coupled directly or indirectly with a pivot wheel or other actuation device on the handling device, by means of which the orientation device and thus a transmission rod of a shaft inserted in the handling device can be rotated or torque can be transmitted to it.

Thus several functions can be integrated in the orientation device, in particular the automatic rotation of a proximal end of a transmission rod into a predetermined orientation, the locking of the rod coupling and the transmission of torque to an inserted transmission rod. This integration or realization of several functions in the orientation device makes possible an especially easy, low-cost, compact and robust structure of the handling device.

A micro-invasive surgical instrument includes a handling device as described here, a shaft with a proximal end that is configured for detachable coupling with the handling device and a distal end that is mechanically connected or connectable with a tool, and a transmission rod to transmit at least either a force or torque from the handling device to the distal end of the shaft, while the transmission rod comprises on its proximal end a non-rotation-symmetrical shape that corresponds to the shape of the orientation device.

The shaft of the micro-invasive surgical instrument can be straight or curved, rigid or flexible. In the case of a curved or flexible shaft, the transmission rod is, in particular, pliable at least in some parts. The tool particularly includes a grasping, dissecting, biopsy or other type of forceps, a scissors or a needle holder with at least two straight or curved clamps, cutting edges or other jaw members, at least one of which is movable. Alternatively, the tool can include another active device, for example a manipulator with a finger or a finger-shaped device or an electrode in hooked shape or some other form. The transmission rod is particularly configured to transmit a tractive and/or pushing force to the tool on the distal end of the shaft. Alternatively or in addition, the transmission rod can be configured to transmit torque and a rotary movement to the tool. The proximal end of the transmission rod has, in particular, a shape that corresponds to a proximal end of a pass-through opening in the orientation device.

With the characteristics and properties of the handling device and corresponding characteristics and properties of the shaft and transmission rod, as described here, a simple, rapid and reliable installation and efficient use of the micro-invasive surgical instrument are possible.

In particular, the tool on the distal end of the shaft can be rotated or turned around its longitudinal axis by means of torque transmitted by the transmission rod from the handling device to the distal end of the shaft. Rotation of the tool independently of the shaft is thereby possible. For example with a micro-invasive procedure with several instruments with cured shafts in a trocar, each individual tool can be turned independently of the orientation of the curved shaft on whose end the tool is mounted.

A micro-invasive surgical instrument as described here includes in particular a tool on the distal end of the shaft so that the tool includes a curved jaw member.

In particular, the tool includes two or more curved jaw members. As long as a curved jaw member can be pivoted around a pivot axis, it is curved in particular in a plane perpendicular to the pivot axis or in a plane parallel to the pivot axis or in both directions.

Arched or even screw-shaped curved clamps, cutting edges or other jaw members of micro-invasive surgical instruments are especially suited for some applications. With an application of a tool with two curved jaw members, however, contrary to a tool with two equal or similar, straight or essentially straight jaw members, a rotation by more than 90 degrees (up to 180 degrees) can be required to align the tool correctly in relation to an object. Rotatability of a tool with one or more curved jaw members around a longitudinal axis of a shaft of a tool can therefore be especially advantageous.

BRIEF DESCRIPTION OF THE DRAWINGS

Embodiments are presented in greater detail hereinafter with reference to the attached drawings, which are as follows.

DETAILED DESCRIPTION OF THE INVENTION

Figure 1:
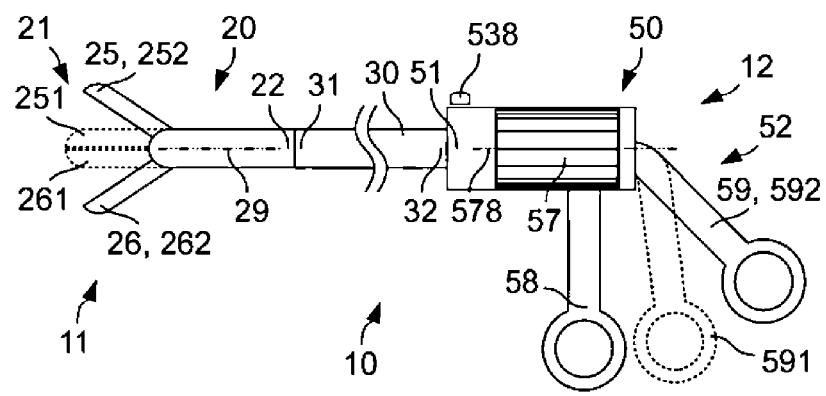
FIG. 1 shows a schematic depiction of a micro-invasive surgical instrument.

FIG. 1 shows a schematic depiction of a micro-invasive surgical instrument 10 with a distal end 11 and a proximal end 12. The micro-invasive surgical instrument 10 includes a tool 20, a shaft 30 and a handling device 50. On the distal end 21 the tool 20 comprises a first movable jaw member 25 and a second movable jaw member 26. The jaw members 25, 26 are shown in FIG. 1 in firm outline in open positions 252, 262 and in dotted lines in closed positions 251, 261. The jaw members 25, 26 can each be straight or essentially straight or can be curved in the direction perpendicular to the plane of projection of FIG. 1 and/or—contrary to the depiction in FIG. 1—in the plane of projection of FIG. 1.

The proximal end 22 of the tool 20 is detachably mechanically coupled with a distal end 31 of the shaft 30. The shaft 30 is shown strongly foreshortened in FIG. 1 and straight for the sake of simplicity. Contrary to the depiction in FIG. 1, the shaft 30 can be level or spatially curved. With a shaft 30 that is within a plane or—even more advantageous for a few applications—spatially curved in shape, the micro-invasive surgical instrument 10 can be suited especially for surgical procedures in which the endoscope and one or more instruments are inserted simultaneously into a body cavity through a single access way.

The proximal end 32 of the shaft 30 is detachably mechanically coupled with the distal end 51 of the handling device 50. The handling device 50 comprises a rotary wheel 57, a first gripping member 58 and a second gripping member 59 for handling the micro-invasive surgical instrument 10. The rotary wheel 57 is provided to control a rotation of the tool 20, in particular the jaw members 25, 26, around a longitudinal axis 29. In the example shown in FIG. 1, the rotary wheel 57 can rotate around an axis 578 that is simultaneously the longitudinal axis of the shaft 30 on its proximal end 32. Alternatively, the axis 578 can be parallel to the longitudinal axis of the shaft 30 on its proximal end 32. In addition, the rotary wheel 57 comprises a surface structure that allows reliable operation or actuation even with gloves, for example the indicated pin in the axial direction. The gripping members 58, 59 in particular—contrary to the strongly stylized shape shown in FIG. 1—are positioned and formed in such a way that medical staff can grip and move the two gripping members 58, 59 in relation to one another with one hand without little fatigue.

At least one of the two gripping members 58, 59 is movable in relation to the other components of the handling device 50. In the example shown in FIG. 1, the first gripping member 58 is rigidly positioned and the second gripping member 59 is movably positioned. The second gripping member 59, in particular, is movable between the first working position 591 shown in dotted lines in FIG. 1 and a second working position 592 indicated in firm lines in FIG. 1. The second gripping member 59 of the handling device 50 is mechanically coupled with the jaw members 25, 26 of the tool 20 in such a way that the jaw members 25, 26 happen to be in their closed positions 251, 261 when the second gripping member assumes its first working position 591, and that the jaw members 25, 26 happen to be in their open positions 252, 262 when the second gripping member 59 assumes its second working position 592.

Figure 2:
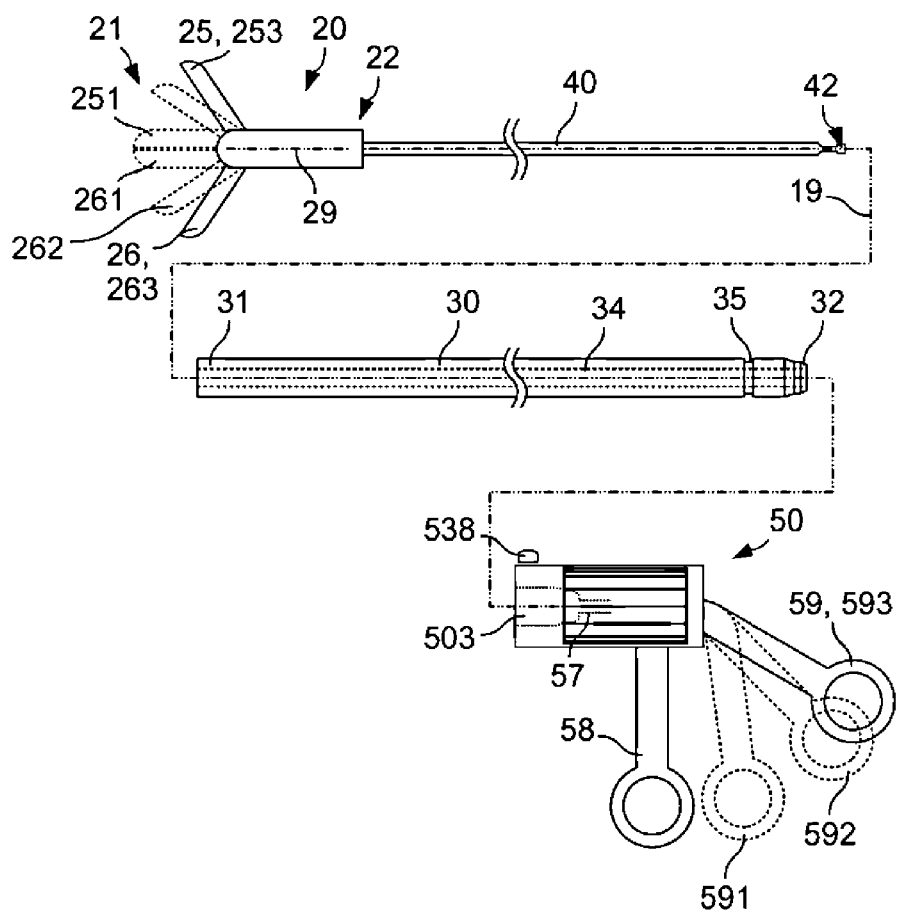
FIG. 2 shows a schematic depiction of the micro-invasive surgical instrument from FIG. 1 in dismantled form.

FIG. 2 shows a schematic depiction of components of the micro-invasive surgical instrument 10 described above with reference to FIG. 1, which can be installed and/or assembled to form an instrument without use of a tool. Likewise, the micro-invasive surgical instrument 10 can be dismantled without a tool into the components illustrated separately in FIG. 2. The broken line 19 that runs through the entire FIG. 2 indicates how these components are to be assembled.

The tool 20 is, in particular, durably connected with a transmission rod 40 that is provided to transmit a force and torque from the handling device 50 to the tool 20. The distal end of the transmission rod 40, which is not shown in FIG. 2, is coupled with the jaw members 25, 26 in such a way that a movement of the transmission rod 40 parallel to the longitudinal axis 29 of the tool 20 causes a synchronous movement of the jaw members 25, 26.

Bayonet coupling devices, not shown in FIG. 2, as well as a locking device coupled with the transmission rod 40 are provided on the proximal end 22 of the tool 20 and on the distal end 31 of the shaft 30. The jaw members 25, 26 are shown in FIG. 2 in firm outline in fully open positions 253, 263 and in dotted lines in the closed and open positions 251, 252, 261, 262 already described above with reference to FIG. 1. If the jaw members 25, 26 happen to be the fully open positions 253, 263, the locking device that is coupled with the jaw members 25, 26 and the distal end of the transmission rod 40 and not shown in FIG. 2 is inactive. In this condition the transmission rod 40 can be inserted in a channel 34 foreseen for the transmission rod 40 in the shaft 30, and the proximal end 22 of the tool and the distal end 31 of the shaft can be detachably mechanically connected or coupled together by the bayonet coupling devices not shown in FIG. 2. In addition, in this unlocked condition a mechanical coupling of the proximal end 22 of the tool 20 and the distal end 31 of the shaft 30 can be released by the bayonet coupling devices that are not shown in FIG. 2.

If the jaw members 25, 26 are in the closed positions 251, 261, in the open positions 252, 262 or in positions situated in between, then the locking device that is coupled with the distal end of the transmission rod 40 and directly with the jaw members 25, 26 is situated in a working position or in a position inside a working range. In the working position or in the positions within the working range, the mechanical coupling of the proximal end 22 of the tool 20 is locked with the distal end 31 of the shaft 30 by the bayonet coupling devices not shown in FIG. 2. If the mechanical connection or coupling of the tool 20 and shaft 30 is locked, the tool 20 and shaft 30 cannot be separated from one another, or not necessarily without disturbance.

Instead of the bayonet coupling devices, the proximal end 22 of the tool 20 and the distal end 31 of the shaft 30 can comprise other coupling devices. In this case too, a locking device is provided on the tool 20 that locks the mechanical connection of the tool 20 and shaft 30 when the jaw members 25, 26 are found in the fully open positions 253, 263.

If the transmission rod 40 is inserted in the channel 34 of the shaft 30 and the proximal end 22 of the tool 20 is mechanically connected or coupled with the distal end 31 of the shaft 30, the proximal end 32 of the shaft 30 with the proximal end 42 of the transmission rod 40 that projects outward with respect to the proximal end 32 of the shaft 30 can be inserted in the handling device 50. For this purpose the handling device 50 comprises a recess 503 as indicated by a dotted line in FIG. 2.

To insert the proximal end 32 of the shaft 30 and the proximal end 42 of the transmission rod 40 in the handling device 50, the second gripping member 59 is first brought into a coupling position 593 as shown in unbroken lines in FIG. 2. If the second gripping member 59 is in the coupling position 593, then a rod coupling inside the handling device 50 but not shown in FIG. 2 is found in a coupling position in which it can receive or release the proximal end 42 of the transmission rod 40. If the proximal end 42 of the transmission rod 40 is inserted entirely in the handling device 50, the rod coupling that is inside the handling device 50 but is not shown in FIG. 2 is mechanically connected or coupled with the proximal end 42 of the transmission rod 40. In so doing, the second gripping member 59, depending on the positions of the jaw members 25, 26 (closed positions 251, 261, open positions 252, 262 or in between), moves into the first working position 591, the second working position 592 or a position between the first working position 591 and second working position 592.

If the proximal end 32 of the shaft 30 is inserted completely into the handling device 50, a bolt that is not shown in FIG. 2 grips in a surrounding groove 35 close to the proximal end 32 of the shaft 30, thus locking the proximal end 32 of the shaft 30 in a foreseen position in the handling device 50. Because of the locking of the proximal end 32 of the shaft 30 in the handling device 50, the mechanical coupling of the proximal end 42 of the transmission rod 40, with the rod coupling that is not shown in FIG. 2, is also indirectly locked in the interior of the handling device 50.

After the locking of the proximal end 32 of the shaft 30 in the handling device 50, and indirectly of the proximal end 42 of the transmission rod 40 in the handling device 50 in the rod coupling not shown in FIG. 2, the micro-invasive surgical instrument 10 is configured as shown in FIG. 1. By moving the second gripping member 59 in relation to the first gripping member 58 between the two working positions 591, 592, the jaw members 25, 26 can be moved between the closed positions 251, 261 and the open positions 252, 262. By rotating the rotary wheel 57 around the axis 578, the jaw members 25, 26 can be rotated around the longitudinal axis 29 of the tool 20.

Contrary to the depictions in FIGS. 1 and 2, the shaft 30 can comprise, close to its proximal end 32, a second rotary wheel that is positioned close to the distal end 51 of the handling device 50 if the proximal end 32 of the shaft 30 is inserted into the handling device 50. The shaft 30 can be rotated around the longitudinal axis of the proximal end 20 of the shaft 30 by means of this rotary wheel, which is not shown in FIGS. 1 and 2. This is particularly significant when the shaft 30 is curved, contrary to the depictions in FIGS. 1 and 2. In this case the curved shaft 30 and the tool 20 can be rotated independently of one another on the distal end 31 of the curved shaft 30.

Through pressure on the unlocking button 538, the bolt, not shown in FIG. 2, can be pushed against the force of a spring and can be disengaged from the groove 35 on the shaft 30. Then the proximal end 32 of the shaft 30 can be removed from the handling device 50. At the same time, the locking of the proximal end 42 of the transmission rod 40, on the rod coupling in the handling device 50 that is not shown in FIGS. 1 and 2, is also released.

Instead of one or—as shown in FIGS. 1 and 2—two movable jaw members 25, 26, the tool 20 can comprise a different active device, in particular a manipulator, for example a finger-shaped manipulator, or an electrode, for example a hook-shaped electrode.

Figure 3:
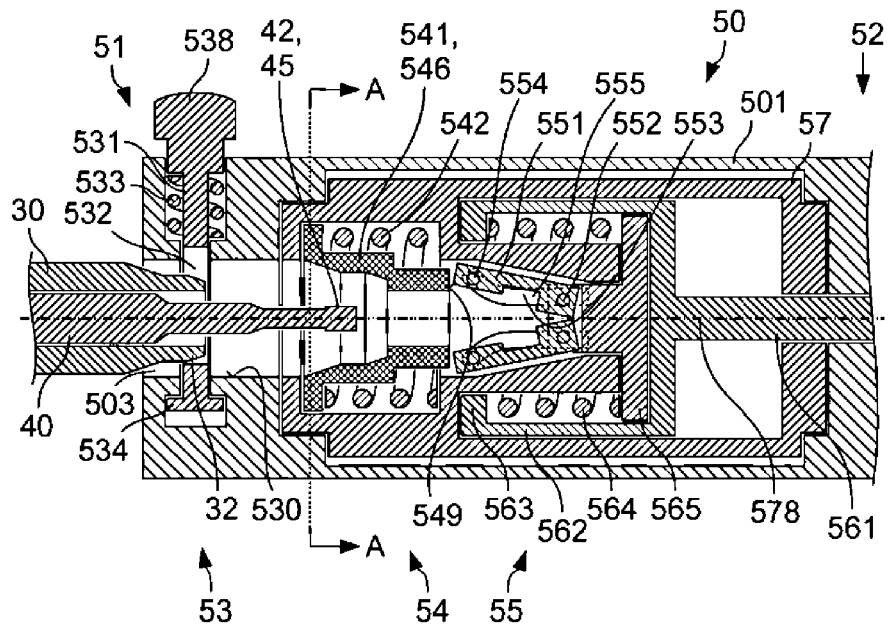
FIG. 3 shows a schematic depiction of a handling device.

FIG. 3 shows a schematic depiction of a section along an embodiment of the handling device 50 of the micro-invasive surgical instrument presented above with reference to FIGS. 1 and 2. The illustrated sectional plane is parallel to the planes of projection of FIGS. 1 and 2 and contains the axis 578 already indicated in FIGS. 1 and 2. The gripping members 58, 59 shown in FIGS. 1 and 2 are not included in FIG. 3.

The handling device 50 includes a housing 501 with the recess 503 that extends from the distal end 51 of the handling device 50 and was already indicated in FIG. 2. The surface of the recess 503 is, in particular, configured essentially as a cylindrical guide surface 530 symmetrical to the axis 578. A proximal end 32 of a shaft 30 and a proximal end 42 of a transmission rod 40 positioned in the shaft 30 are shown in FIG. 3 partly inserted in the recess 503.

The complete insertion of the proximal end 32 of the shaft 30 and of the proximal end 42 of the transmission rod 40 into the handling device 50, the locking of the shaft 30 on the handling device 50 and the mechanical coupling of the proximal end 42 of the transmission rod 40 with elements of the handling device 50 are described below with reference to FIGS. 6 through 8. First, with reference to FIG. 3, only the components or elements of the handling device 50 are described.

A few components or elements of the handling device 50, which are each presented in FIGS. 3 and 6 through 8 as in a single piece because they each constitute rigid mechanical units in themselves in the handling device 50, can each be composed of several form-locked, force-locked or firmly bonded joined elements, contrary to the illustrations, for example for technical manufacturing reasons.

The handling device 50 includes a shaft coupling 53 close to the distal end 51. The shaft coupling 53 is configured by the guide surface 530 and a locking unit to lock or block the shaft 30 in the handling device 50. The locking device includes a bolt 531 that extends essentially perpendicularly to the axis 578 and can slide in linear manner perpendicularly to the axis 578 within a predetermined area.

At one end the bolt 531 comprises a collar 534 in a hollow space in the housing 501 of the handling device 50, and the shape of the collar 534 and the shape of the hollow space restrict the linear slidability of the bolt 531. On the other end the bolt 531 comprises an unlocking button 538, which extends with respect to the outer contour of the housing 501 of the handling device 50. The bolt 531 comprises an opening 532, which is adapted to the outer contour of the cross-section of the shaft 30. A spring 533 between an indentation on the housing 501 of the handling device 50 and an indentation on the bolt 531 pushes the bolt 531 into the position shown in FIG. 3.

By pressure on the unlocking button 538 or by the impact of a conical portion on the shaft 30 on the border of the opening 532 in the bolt 531, the bolt 531 can be pushed in linear manner against the force of the spring 533 all the way to a position in which the border of the opening 532 in the bolt 531 no longer protrudes into the recess 503. In this position of the bolt 531, the shaft 30 can be inserted into the recess 503 or removed from it.

The handling device 50 further includes a control and orientation device 54, designated hereinafter as orientation device, and a rod coupling 55 inside the essentially drum-shaped pivot wheel 57. The orientation device 54 and the rod coupling 55 are configured to be rotated together with the pivot wheel 57 and the axis 578. The orientation device 54 and rod coupling 55 are therefore rigidly connected with the pivot wheel 57 with respect to rotation around the axis 578. Both the orientation device 54 and the rod coupling 55, however, can be slid inside the handling device and in relation to the pivot wheel 57 in axial direction or parallel to the axis 578, each within a predetermined area.

The orientation device 54 includes a slide bar 541, which in FIG. 3 is shown in a distal installation position 546. Between a collar of the slide bar 541 and the pivot wheel 57, a spring 542 is positioned that holds the slide bar 541 elastically in the installation position 546. The slide bar 541 and pivot wheel 57, in particular, on the proximal end of the slide bar 541 in the surrounding of a proximal front surface 549 of the slide bar 541, comprise surfaces that are adjacent with one another and are not rotation symmetrical to the axis 578. The slide bar 541 is thereby held in a predetermined orientation in relation to the pivot wheel 57, independently of its position in the axial direction with respect to rotation around the axis 578.

The rod coupling 55 includes two gripping clamps 551 that are positioned symmetrically to the axis 578 and that are jointedly affixed by joints 552 to a force transmission component 565. Each gripping clamp 551 comprises a recess 553 with a shape that corresponds to the form of a claw 45 on the proximal end 42 of the transmission rod 40. In addition, each gripping clamp 551 comprises a guide pin 554 whose axis is perpendicular to the sectional plane of FIG. 3. Every end of each of the guide pins 554 engages in each case in an associated control groove 555 in the pivot wheel 57. Besides the two control grooves 555 shown in FIG. 3, two control grooves not shown in FIG. 3 behind the sectional plane of FIG. 3 are foreseen on the pivot wheel 57 and are mirror symmetrical to the control grooves 57 shown in FIG. 3 with respect to the sectional plane of FIG. 3. The control grooves 555 are curved at least in portions. In a linear sliding of the joints 552 of the gripping clamps 551 parallel to the axis 578, the control grooves 555 cause pivotal movements of the gripping clamps 551, which are described below with reference to FIGS. 6 through 8.

Inside the pivot wheel 57, in addition, a rod 561 and a beaker-shaped component 562 are positioned. The rod 561 and the beaker-shaped component 562 are rigidly interconnected and can slide parallel to the axis 578 inside the pivot wheel 57. A pressure spring 564 is positioned between a collar 563 of the beaker-shaped component 562 pointing radially inward and a collar of the force transmission component 565 pointing radially outward. The pressure spring 564 restricts a tractive force that can be transmitted from the rod 561 via the beaker-shaped component 562, the pressure spring 564, the force transmission component 565 and the gripping clamps 551 to a proximal end 42 of a transmission rod 40 that is coupled with the gripping clamps 551.

The proximal end of the rod 561, which is not shown in FIG. 3, is—for example by means of a connection rod— coupled with the second gripping member 59, described above with reference to FIGS. 1 and 2, in such a way that a pivot movement of the second gripping member 59 causes a linear movement of the rod 561 and of the rod coupling 55 parallel to the axis 578.

Figure 4:
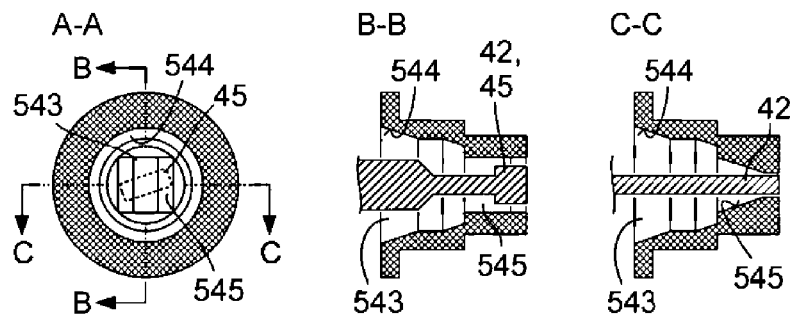
FIG. 4 shows a schematic depiction of an orientation device.
Figure 5:
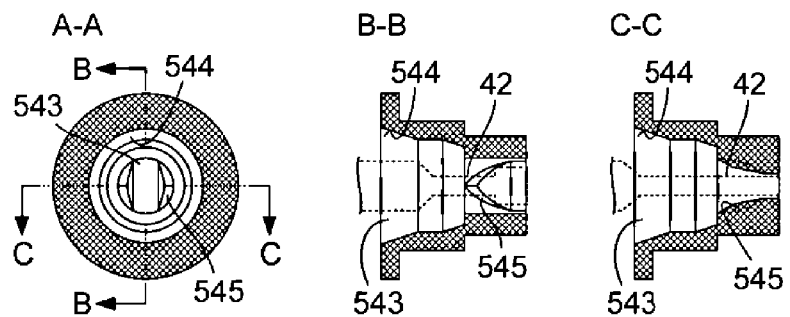
FIG. 5 shows a schematic depiction of an additional orientation device.

Before a closer discussion of the functioning of the rod coupling 55 with reference to FIGS. 6 through 8, two different embodiments of the slide bar 541 are described with reference to FIGS. 4 and 5. FIGS. 4 and 5 each show a section along the sectional plane A-A indicated in FIG. 3 at the left, and sections along the planes B-B and C-C in the center and at right, which are indicated in FIGS. 4 and 5 at the left in depictions of the section along the plane A-A. The sectional plane A-A is perpendicular to the axis 578 shown in FIG. 3. The sectional planes B-B and C-C each contain the axis 578. All sectional planes A-A, B-B and C-C are perpendicular to one another.

Both embodiments of the slide bar 541 illustrated in FIGS. 4 and 5 comprise a pass-through opening 543. In a distal portion shown in each case at the left in FIGS. 3 through 5, the surface of the pass-through opening 543 is configured as a partly conical support surface 544 for the proximal end 32 of the shaft 30. The support surface 544 is rotation symmetrical or essentially rotation symmetrical to the axis 578 and adapted to the shape of the proximal end 32 of the shaft 30 shown in FIG. 3.

In the embodiment of the slide bar 541 illustrated in FIG. 4, the pass-through opening 543 comprises in a proximal portion two flat and essentially rectilinear gliding surfaces 545, which face one another in wedge shape running from distal to proximal. The gliding surfaces 545 form with their distal edges an approximately square cross-section of the pass-through opening 543. With their proximal edges the gliding surfaces 545 form a narrow rectilinear cross-section, which is adapted to the cross-section of the claw 45 of the proximal end 42 of the transmission rod 40 illustrated in FIG. 3.

Shown in broken lines at the left in FIG. 4, in the section along the plane A-A, is the cross-section of the claw 45 on the proximal end 42 of the transmission rod in the orientation illustrated in FIG. 3. This orientation of the proximal end 42 and of the claw 45 does not correspond to the orientation determined by the cross-section of the pass-through opening 543 on the proximal edges of the glide surfaces 545. In the center and at right in FIG. 4, in the sections along the planes B-B and C-C, the proximal end 42 of the transmission rod is shown with the claw 45 in the orientation that is determined by the cross-section of the pass-through opening 543 at its proximal end.

In the section along the plane B-B, it can be recognized that the distal end 42 of the transmission rod 40, in particular the claw 45, is not narrowly contained in the direction parallel to the sectional plane B-B and perpendicular to the axis 578. In the section along the plane C-C, it can be recognized that the distal end 42 of the transmission rod 40 is contiguous with the slide bar 541 in the direction parallel to the sectional plane C-C- and perpendicular to the axis 578, thus determining the orientation of the proximal end 42 of the transmission rod 40. At the right in FIG. 4, in the section along the plane C-C, it can be recognized that the transmission rod 40 is flattened in a large area adjoining the proximal end 42 to allow it to be pushed even farther in the proximal direction, starting from the position with respect to the slide bar 541 as shown in the center and at right in FIG. 4.

FIG. 5 shows an alternative embodiment of the slide bar 541 in which the cross-section of the pass-through opening 543 of the slide bar 541 is modified in a proximal area from a circular to a rectilinear shape. Contrary to the embodiment in FIG. 4, four glide surfaces 545 are provided, which are not rectilinear and not level. The glide surfaces 545, similarly as in the embodiment in FIG. 4, in inserting a proximal end 42 of a transmission rod 40 from the distal to the proximal direction, cause a rotation of the transmission rod from a freely chosen original orientation to an orientation determined by the slide bar 541. To allow the glide surfaces 545 to be displayed also in sections B-B and C-C, FIG. 5 depicts the contours of the transmission rod 40 merely in broken lines.

Figure 6:
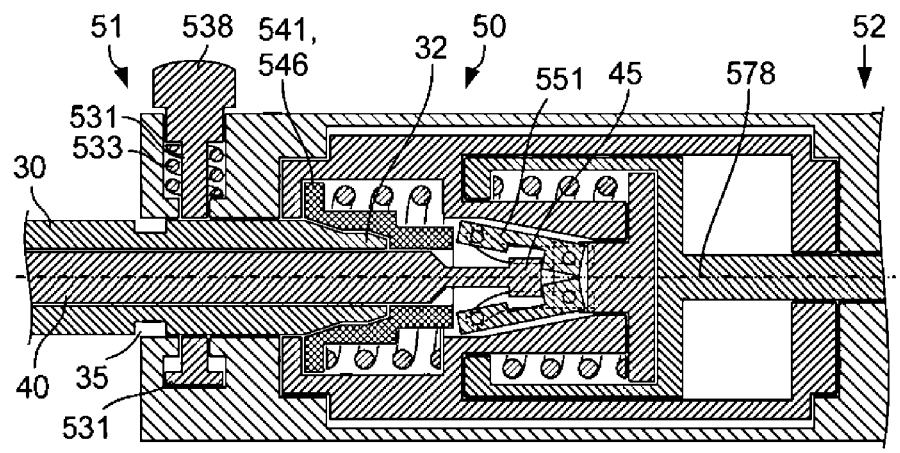
FIG. 6 shows an additional schematic depiction of the handling device from FIG. 3.
Figure 7:
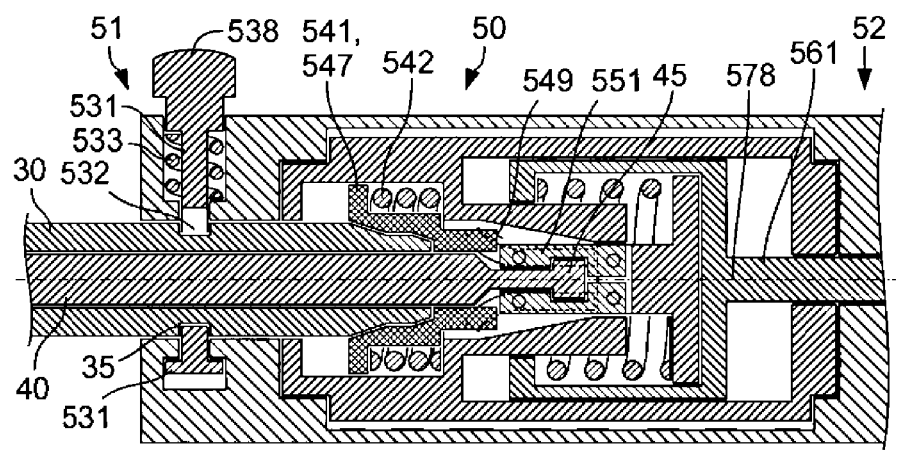
FIG. 7 shows an additional schematic depiction of the handling device from FIG. 3.
Figure 8:
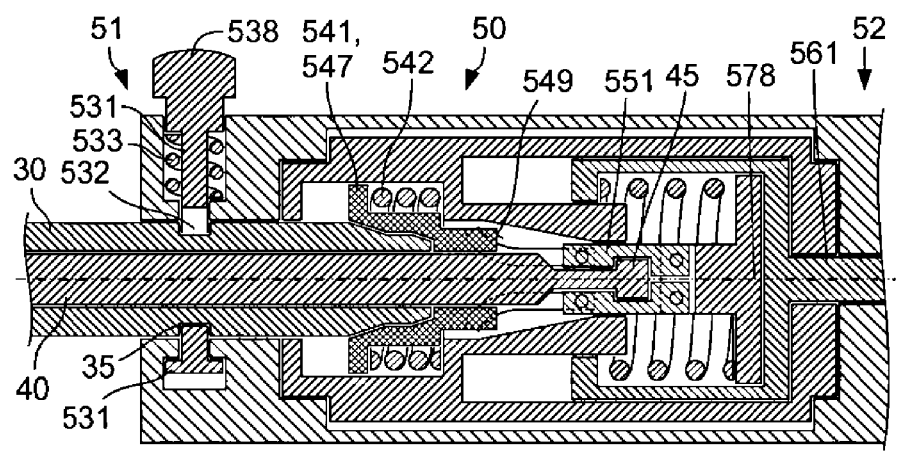
FIG. 8 shows an additional schematic depiction of the handling device from FIG. 3.

FIGS. 6, 7 and 8 show schematic depictions of the handling device 50, with the shaft 30 and transmission rod 40 in other positions with respect to the handling device 50. The sectional planes depicted in FIGS. 6, 7 and 8 correspond to the sectional plane of FIG. 3. To avoid cluttering FIGS. 6 through 8, reference numbers are displayed only for the most important characteristics.

In the situation illustrated in FIG. 6, the shaft 30 and transmission rod 40 are inserted so far into the handling device 50 that the proximal end 32 of the shaft 30 is contiguous with the slide bar 541. Upon sliding the proximal end 32 of the shaft 30 into the handling device 50, the bolt 531 upon touching a conical portion of the shaft 30 with the edge of the opening 532 in the bolt 531, was pushed against the force of the spring 533 perpendicular to the axis 578 into the position shown in FIG. 6.

The claw 45 on the proximal end 42 of the transmission rod 40 is already situated between the gripping clamps 551, which however are still found in an opened installation position.

In the situations shown in FIGS. 7 and 8, the shaft 30 is completely pushed into the handling device 50. The bolt 531 engages in the surrounding groove 35, already visible in FIG. 6, on the outermost surface of the shaft 30. By the spring 533, the bolt 531 is held in this position locking the shaft 30. Locking by the bolt 531 can be released only by pressure on the unlocking button 538. With the shaft 30 in the locked position shown in FIGS. 7 and 8, the slide bar 541 is pushed against the force of the spring 542 into its working position 547 and is held there by the shaft 30.

The situations shown in FIGS. 7 and 8 are distinguished by the fact that the rod 561, the rod coupling 55 and the transmission rod 40 are found in different positions. In particular, in the situation illustrated in FIG. 7, the jaw members 25, 26 shown in FIG. 1 are situated in their open positions 252, 262 and the second gripping member 59 is in the second working position 592. In the situation shown in FIG. 8, the jaw members 25, 26 shown in FIG. 1, in particular, are situated in their closed positions 251, 261 and the second gripping member 59 is situated in its first working position 591.

It can be recognized in FIG. 7 that the gripping clamps 551 are contiguous with the proximal front surface 549 of the slide bar 541. The slide bar 541 or its proximal front surface 549 thus forms a mechanical stop for the gripping clamps 551. The gripping clamps 551 therefore cannot be pushed farther in the distal direction with respect to their position shown in FIG. 7. The gripping clamps 551 thereby remain controlled by the control grooves 555, in which the guide pins 554 of the gripping clamps 551 engage (see also FIG. 3) in the closed working positions shown in FIGS. 7 and 8. In the closed working positions shown in FIGS. 7 and 8, the gripping clamps hold the claw 45 on the proximal end 42 of the transmission rod 40 in form-locked connection and with little play. Only after unlocking the shaft 30 by pressure on the unlocking button 538 can the shaft 30, the slide bar 541 and thus also the gripping clamps 551 be pushed so far in the distal direction that the gripping clamps 551, controlled by the control grooves 555, reach the installation positions shown in FIG. 6 and release the claw 45.

A further consequence of the mechanical stop of the gripping clamps 551 on the proximal front surface 549 of the slide bar 541 is that the transmission rod 40 held by the gripping clamps 551 cannot be pushed so far in the distal direction that the jaw members 25, 26 reach the fully open positions 253, 263 shown in FIG. 2. Thus, as shown above with reference to FIG. 2, the tool 20 likewise cannot be separated from the distal end 31 of the shaft 30.

In the embodiment presented with reference to FIGS. 3 through 8, the slide bar 541 comprises several functions. One function of the slide bar 541 is, during the insertion of the proximal end 42 of the transmission rod 40 into the handling device 50, to rotate the proximal end 42 of the transmission rod 40 into a predetermined orientation. An additional function of the slide bar 541 consists in restricting the slidability of the rod coupling 55 and of the transmission rod 40 in the distal direction when the shaft 30 is locked by means of the bolt 431 in the handling device 50. Restriction of slidability of the rod coupling 55 by the slide bar 541 causes a locking of the rod coupling 55 in the condition shown in FIGS. 7 and 8 in which the rod coupling 55 holds the proximal end 42 of the transmission rod 40. In addition, restriction of slidability of the rod coupling by the slide bar 541 also has the effect that the transmission rod 40 coupled with the rod coupling 55 cannot be pushed so far in the distal direction that the locking of the mechanical coupling, described above with reference to FIGS. 1 and 2, could be released by the tool 20 and the shaft 30.

Alternatively, the handling device 50 and particularly the orientation device 54 are configured in such a way that the only result is a rotation of a proximal end 42 of a transmission rod inserted into the handling device 50 into a predetermined orientation. For this purpose, a component similar to the slide bar 541 with respect to its rotating characteristics can be rigidly positioned in the pivot wheel 57. This component, which is rigidly connected with the pivot wheel 57 or produced as a single unit with it, comprises, in particular, glide surfaces similar to the glide surfaces 545 described above with reference to FIGS. 4 and 5, to rotate the proximal end 42 of the transmission rod 40.

In the embodiments described above, the transmission rod 40 is configured both to transmit a translational movement in a direction parallel to the shaft 30 or to its longitudinal axis and to a corresponding pulling and/or pushing force and to transmit a rotational movement and corresponding torque. A force acting in the longitudinal direction is transmitted by form-locking between the rod coupling 55 of the handling device 50 and the proximal end 42 of the transmission rod 40. For this purpose, in particular, the gripping clamps 551 of the rod coupling 55 enclose the claw 45 on the proximal end 42 of the transmission rod 40 and receive it in their recesses 553. A force acting in the longitudinal direction can, alternatively or in addition, be transmitted by force locking or frictional locking between the rod coupling 55 and the proximal end 42 of the transmission rod. In particular, a force acting in the longitudinal direction, because of force locking or frictional locking, can also be transmitted when the proximal end 42 of the transmission rod 40 in the area of the rod coupling 55 has a constant cross-section instead of the claw 45.

Contrary to the description provided above with reference to the drawings, the transmission rod 40 and rod coupling 55 can be configured only to transmit torque. This can be the case, in particular, when the tool 20 on the distal end 31 of the shaft 30 can rotate only around the longitudinal axis of the distal end 31 of the shaft 30 or around another axis. For example, the tool 20 includes a finger-shaped or other manipulator of an electrode in hook or loop form or in some other shape. In particular when only torque is to be transmitted between the transmission rod 40 and the rod coupling 55, the proximal end 42 of the transmission rod 40 can have a constant cross-section, contrary to the depictions in FIGS. 2 through 8.

What is claimed is:

1. A handling device for a micro-invasive surgical instrument, having:
    a gripping device for manual holding and guiding of the handling device;
    a shaft coupling detachably mechanically coupling the handling device with a proximal end of a shaft;
    a rod coupling that at least either slides or rotates in the handling device to detachably mechanically couple the handling device with a proximal end of a transmission rod, said transmission rod either slides or rotates in said shaft; and
    an orientation device to rotate said proximal end of said transmission rod inserted in the handling device into a predetermined orientation or into one of several predetermined orientations.

2. The handling device according to claim 1, wherein the orientation device comprises a pass-through opening, which extends in the direction from distal to proximal, such that the cross-section of the pass-through opening continues to vary at least in portions going from distal to proximal.

3. The handling device according to claim 1, wherein the orientation device can slide in relation to the rod coupling between a predetermined distal installation position and a predetermined proximal working position.

4. The handling device according to claim 3, wherein the handling device is configured in such a way that the orientation device in the predetermined proximal working position holds the rod coupling locked.

5. The handling device according to claim 4, in addition having:
    a shaft locking device for locking the shaft to the shaft coupling, such that the handling device is configured in such a way that the shaft locked by the shaft locking device to the shaft coupling holds the orientation device in the predetermined proximal working position in which the orientation device has locked the rod coupling.

6. The handling device according to claim 1, wherein the rod coupling includes a movable gripping clamp to hold a proximal end of a transmission rod, such that the rod coupling is configured in such a way that the gripping clamp, with the rod coupling in a predetermined installation position, can receive or release a proximal end of a transmission rod and can hold a proximal end of a transmission rod in a predetermined working range of positions of the rod coupling.

7. The handling device according to claim 6, in addition having:

a guide pin and a control groove, such that either the guide pin or the control groove is positioned on the gripping clamp, and such that the guide pin engages in the control groove in order to hold the gripping clamp in various positions depending on the position of the rod coupling.

8. The handling device according to claim 1, wherein
the orientation device can rotate in relation to the handling device around an axis,
the orientation device in addition is configured to transmit torque to the transmission rod coupled with the rod coupling.

9. A micro-invasive surgical instrument having:
a handling device, having:
- a gripping device for manual holding and guiding of the handling device;
- a shaft coupling detachably mechanically coupling the handling device with a proximal end of a shaft;
- a rod coupling that at least either slides or rotates in the handling device to detachably mechanically couple the handle device with a proximal end of a transmission rod, said transmission rod either slides or rotates in said shaft;
- an orientation device to rotate said proximal end of said transmission rod inserted in the handling device into a predetermined orientation or into one of several predetermined orientations;

wherein a distal end of the shaft is mechanically connected or connectable with a tool; and
the transmission rod transmits at least either a force or a torque from the handling device to the distal end of the shaft, such that the transmission rod comprises on its proximal end a non-rotation-symmetrical shape that corresponds to the shape of the orientation device.

10. The micro-invasive surgical instrument according to claim 9, having a tool on the distal end of the shaft, such that the tool comprises a curved jaw member.

* * * * *